United States Patent [19]
O'Lenick, Jr.

[11] Patent Number: 5,243,028
[45] Date of Patent: Sep. 7, 1993

[54] SILICONE PROTEIN POLYMERS

[75] Inventor: Anthony J. O'Lenick, Jr., Lilburn, Ga.

[73] Assignee: Siltech Corporation, Toronto, Canada

[21] Appl. No.: 851,057

[22] Filed: Mar. 16, 1992

Related U.S. Application Data

[63] Continuation-in-part of Ser. No. 767,402, Sep. 30, 1991, Pat. No. 5,100,956, which is a continuation-in-part of Ser. No. 546,358, Jun. 27, 1990, Pat. No. 5,070,171.

[51] Int. Cl.$^5$ .................. C07K 3/08; C07K 15/10; C07K 17/00
[52] U.S. Cl. .................. 530/375; 525/54.1; 528/33; 530/378; 530/410; 530/816; 556/450
[58] Field of Search .......... 525/54.1, 54.11, 474; 528/33; 556/450; 530/375, 378, 406, 410, 815, 816

[56] References Cited

U.S. PATENT DOCUMENTS

| | | | |
|---|---|---|---|
| 4,725,645 | 2/1988 | Anteunis et al. | 525/54.11 |
| 4,929,670 | 5/1990 | Billmers et al. | 525/54.1 |
| 5,070,171 | 12/1991 | O'Lenick, Jr. | 528/33 |
| 5,100,956 | 3/1992 | O'Lenick, Jr. | 525/54.1 |
| 5,210,133 | 5/1993 | O'Lenick, Jr. | 530/406 |

*Primary Examiner*—Jeffrey E. Russel

[57] ABSTRACT

The present invention relates to a series of novel silicone proteins which are high substantive to fiber and hair. They are cationic materials which contain an ester linkage. A chloroester of a dimethicone copolyol is reacted with the amino group of a protein or amino acid. The compounds contain both a silicone portion and protein portion in a covalent bone one molecule. Since the compounds of the present invention are high molecular weight silicone polymers, they have a high degree of oxidative stability, even at elevated temperatures and are nonirritating to skin and eyes. The proteins of the present invention plate out on and form a film on the surface of hair skin and textile fibers. In addition, these compounds are non volatile and exhibit a inverse cloud point. These combination of properties makes these polymers ideally suited for use in personal care applications.

8 Claims, No Drawings

SILICONE PROTEIN POLYMERS

RELATED APPLICATIONS

This application is a continuation in part of copending application Ser. No. 767,402 filed Sep. 30, 1991 which is now U.S. Pat. No. 5,100,956which is a continuation in part of copending application Ser. No. 07/546,358, filed Jun. 27, 1990 now U.S. Pat. No. 5,070,171.

BACKGROUND OF THE INVENTION (1) Field of the Invention

The present invention relates to a series of novel silicone proteins which are high substantive to fiber and hair. The compounds contain both a silicone portion and protein portion in a covalent bond in one molecule. Since the compounds of the present invention are high molecular weight silicone polymers, they have a high degree of oxidative stability, even at elevated temperatures and are nonirritating to skin and eyes. The proteins of the present invention plate out on and form a film on the surface of hair skin and textile fibers. These compounds are non volatile and exhibit a inverse cloud point. These combination of properties makes these polymers ideally suited fo use in personal care applications. The silicone proteins of the present invention are highly substantive to kertinous materials like hair and skin. Prior to the compounds of the present invention proteins lacked the desired substantivity and were easily removed from the hair and skin to which they are applied.

The compounds of the present invention, unlike the compounds of the copending application, are based upon raw materials which are prepared by the esterification reaction of the pendant hydroxyl group on a silicone polymer with monochloroacetic acid followed by the reaction of the chloro ester with a protein or amino acid's amino group. The compounds of the present invention contain no phosphorus which can be of concern in many areas where there are bans on phosphate compounds. In addition they are cationic, not amphoteric in structure, making them more substantive to hair, fiber and skin.

The technology used to produce the silicone proteins of the present invention is very flexible and allows us to prepare permformance tailored molecules for specific applications.

(2) Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emuslsions are generally prepared with contain silicone dispersed in micelles. While this methods of application is easier for processing, much of the oil stays in the surfactant micelle and never gets deposited on the fiber. That which does deposit on the fiber surface remains there by hydrophobic binding, not ionic bonding. Since the polydimethylsiloxane is not ionically bonded the effect is very transient. The product is removed with one washing.

U.S. Pat. Nos. 3,856,893 and 3,928,509 both issued to Diery disclose the basic technology used to make phosphobetaines. Later, amido and imidazoline based phopshobetaines were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaines. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetinaes based upon phosphorous acid salts. These compounds can be prepared by the reaction of a phosphorous acid salt, one equivalent of epichlorohydrin and one equivalent of a tertiary amine.

U.S Pat. No. 4,261,911 issued in 1981 to Lindemann et al teaches the utilization of phosphobetaines based upon phosphorous acid. These compounds are useful as surfactants.

U.S. Pat. No. 4,283,542 issued in 1981 to O'Lenick and Mayhew teaches the process technology used for the preparation of phosphobetaines. These compounds can be prepared by the reaction of a phosphate salt, one equivalent of epichlorohydrin and one equivalent of tertiary amine.

U.S. Pat. No. 4,336,386 issued in 1982 to O'Lenick and Mayhew teaches the technology for the preparation of imidazoline derived phosphobetaines based upon phosphorous acid salts. These compounds can be prepared by the reaction of a phophorous acid salt, one equivalent of epichlorohydrin and one equivalent of an imidazoline.

U.S. Pat. No. 4,503,002 which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

THE INVENTION (1) Object of the Invention

It is the object of the present invention to provide a series of novel silicone phosphorus free proteins which is cationic rather than amphoteric and are highly substantive to hair and skin, have an inverse cloud point and are substantive to the surface of fibers.

Still another object of the present invention is to provide a series of silicone proteins which have differing solubilities in water and organic solvents. This is achieved by selection of the silicone polymer used as a raw material and the protein chosen for preparation of the silicone protein polymer.

Application of the compounds of the invention can be from solvent, aqueous dispersion or solution, or applied neat in these processes.

The chloro-ester containing silicone polymers, suitable as raw materials, in a preferred embodiment, contain varying amounts of ethylene oxide, propylene oxide or butylene oxide or mixture thereof. The presence of the oxide in the silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to skin, hair and fiber.

SUMMARY OF THE INVENTION

The present invention relates to a series of novel silicone ester protein polymers, which are phosphorous free and phosphate free. These compounds have one or more pendant ester functional group connected to the amino group in a protein. The amino group typically will be introduced by the hydrolysis of various naturally occurring proteins. Hence the products are polymers having both a polymeric protein and polymeric silicone group present on the same molecule. The silicone polymer by virtue of this unique pendant group is highly substantive and non irritating to eyes and skin and deposits on fiber surfaces and form effective surface modifying finishes. The compounds of the present invention are therefore very well suited to applications in the personal care market.

Proteins are materials which play a critical role in all biological processes. They are natural products and have enjoyed increasing use in personal care products as conditioners, humectants and softeners. Natural proteins, which are high molecular weight polymers, are generally hydrolyzed into lower molecular weight proteins to obtain water solubility. The water solubility results in easier formulating, but the soluble proteins are less substantive to hair and skin. Consequently, the water soluble proteins end up washed off the substrate being treated. The compounds of the present invention are far more substantive since they have silicone in the molecule. Not only is the silicone more substantive to the skin and hair, the presence of alkylene oxide in the silicone polymer in a preferred embodiment results in a protein with an inverse cloud point. The silicone protein becomes insoluble above this temperature and is more substantive to the hair and skin. This suggests the use of these materials in treatment products where heat is applied, like hot oil treatments.

Amino acids are the basic structural units of proteins. An amino acid has both an amino group and a carboxyl group.

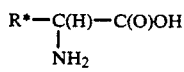

The amino acids are well known to those skilled in the art.

| Amino Acid | R* |
| --- | --- |
| Alanine | $-CH_3$ |
| Arginine | $-(CH_2)_3-N(H)-C(=NH)-NH_2$ |
| Asparagine | $-CH_2-C(O)-NH_2$ |
| Aspartic Acid | $-CH_2-C(O)OH$ |
| Glutamic Acid | $CH_2-CH_2-C(O)OH$ |
| Glycine | $-H$ |
| Histidine | (structure) |
| Isoleucine | $-CH(CH_3)-CH_2-CH_3$ |
| Leucine | $-CH_2-CH(CH_3)-CH_3$ |
| Lysine | $-(CH_2)_4-NH_2$ |
| Methionine | $-CH_2-CH_2-S-CH_3$ |
| Phenylalanine | (structure) |
| Proline | (structure) |
| Serine | $-CH_2(OH)$ |
| Threonine | $-CH(OH)-CH_3$ |
| Tryptophan | (structure) |
| Tyrosine | (structure) |
| Valine | $-CH(CH_3)-CH_3$ |

In proteins the carboxyl group of one amino acid is joined to the amino group of another amino acid in an amide bond. When this amide bond is in a protein it is called a. Many amino acids are joined are joined in peptide bonds to form a polypeptide chain. This polypeptide chain is what we commonly call a protein. The polypeptide has free amino group and a free carboxyl group present.

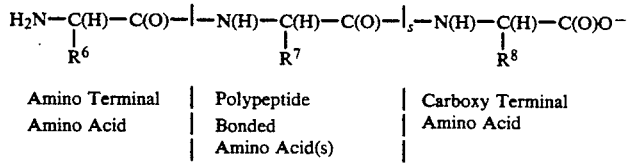

| Amino Terminal Amino Acid | Polypeptide Bonded Amino Acid(s) | Carboxy Terminal Amino Acid | s is an integer from 7 to 5,000, giving the protein a molecular weight of between 1,000 EMWU and 500,000 EMWU (EMWU is equivalent molecular weight units)

The compounds of the present invention are dependant upon the reaction of the terminal amino group in the protein with a reactive silicone intermediate which results in functionalizing of the amino group.

It will be clearly understood that the polypeptide bonded amino acids can be any combination of the amino acids listed above in any order.

The silicone protein is prepared by the reaction of an intermediate conforming to the following structure;

R—O—C(O)—CH$_2$—Cl wherein;
R is

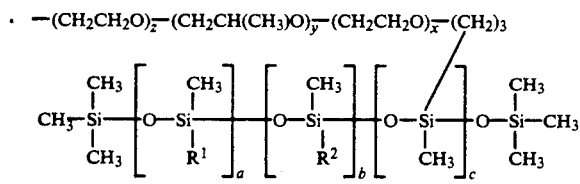

a is an integer from 0 to 200;
b is an integer from 0 to 200;
c is an integer from 1 to 200;
R$^1$ is selected from the group consisting of —(CH$_2$)$_n$CH$_3$ and phenyl;
n is an integer from 0 to 10;

R$^2$ is —(CH$_2$)$_3$—(OCH$_2$CH$_2$)$_x$—(OCH$_2$CH(CH$_3$))$_y$—(OCH$_2$CH$_2$)$_z$—OH;

x, y and z are integers and are independently selected from 0 to 20;

R$^6$, R$^7$, and R$^8$ represent the side chains of amino acids.

The reaction sequence needed to produce the compounds of the present invention starts with a dimethicone copolyol which is esterified with monochloroacetic acid, to produce a chloro silicone ester intermediate.

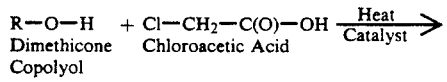

wherein
R is

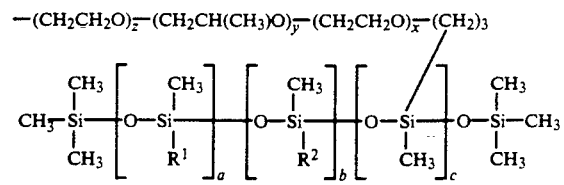

a is an integer from 0 to 200;
b is an integer from 0 to 200;
c is an integer from 1 to 200;
R$^1$ is selected from —(CH$_2$)$_n$CH$_3$ and phenyl;
n is an integer from 0 to 10;
R$^2$ is —(CH$_2$)$_3$—(OCH$_2$CH$_2$)x—(OCH$_2$CH(CH$_3$))y—(OCH$_2$CH$_2$)z—OH;

x, y and z are integers and are independently selected from 0 to 20.

The dimethicone copolyol materials are items of commerce available from Siltech Inc. Norcross, Ga.

PREFERRED EMBODIMENT

In one embodiment the protein is of nonanimal source such as wheat, soya or vegetable.

In still another preferred embodiment the x, y and z are each zero.

In still another preferred embodiment the sum of x+y+z is greater than 1.

EXAMPLES

DIMETHICONE COPOLYOLS

The esters used as raw materials for the preparation of the compounds of the present invention are prepared by reaction of a hydroxyl containing silicone polymer with chloroacetic acid.

One method of preparing the reactive hydroxyl containing silicone polymer is to react silanic hydrogen containing polymer with allyl alcohol or allyl alcohol alkoxylate monomer.

Procedures involving this reaction are well known to those skilled in the art. U.S. Pat. No. 4,083,856 describe suitable processes.

EXAMPLES

Vinyl Intermediate Compounds

Compounds of this class are prepared by alkoxylation of allyl alcohol using methods well known to those skilled in the art. The following are some of the many compounds which can be used to make the products of this invention.

| CH$_2$=CH—CH$_2$—O—(CH$_2$—CH$_2$—O)x—(CH$_2$—CH(CH$_3$)—O)y—(CH$_2$—CH$_2$—O)z—H | | | | |
|---|---|---|---|---|
| Designation | x | y | z | Molecular Weight |
| A | 3 | 0 | 0 | 189 |
| B | 9 | 27 | 3 | 2,178 |
| C | 11 | 3 | 0 | 718 |
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (*Silicone*

*Alkylene Oxide Copolymers As Foam Control Agents*) WO 86/0541 by Paul Austin (Sep. 25, 1986) p. 16 (examples 1 to 6) is simply one of many references which teaches how to make the following intermediates shown.

Hydrosilation of Intermediates

Silanic Hydrogen Containing Compounds $$CH_3-\underset{\underset{M}{\overset{\overset{CH_3}{|}}{Si}}}{\overset{CH_3}{|}}-O-\underset{\underset{D}{\overset{\overset{CH_3}{|}}{Si}}}{\overset{CH_3}{|}}-O-\underset{\underset{D'}{\overset{\overset{H}{|}}{Si}}}{\overset{CH_3}{|}}-O-\underset{\underset{M}{\overset{\overset{CH_3}{|}}{Si}}}{\overset{CH_3}{|}}-CH_3$$

Group Designations

| Example | Austin Example | Group Designation | Average Molecular Weight | Equivalent Molecular Weight |
|---|---|---|---|---|
| 1 | 1 | $MD_{20}D'_{3.2}M$ | 1,850 | 551 |
| 2 | 4 | $MD_{160}D'_5M$ | 24,158 | 4,831 |
| 3 | 6 | $MD_{20}D'_{10}M$ | 2,258 | 225 |

Hydrosilation Compounds

The hydrosilation reaction used to make the compounds of this invention are well known to those skilled in the art. Reference; International Publication (*Silicone Alkylene Oxide Copolymers As Foam Control Agents*) WO 86/0541 by Paul Austin (Sep. 25, 1986) p. 19.

EXAMPLE 4

To a 22 liter three necked round bottom flask fitted with a mechanical agitator, thermometer with a Thermo-watch temperature regulator, nitrogen sparge tube vented reflux condenser and heating mantle is added 189.0 grams of Vinyl Intermediate Example #A. Next add 225 grams of Silanic Hydrogen Containing Compound Example #3 and 3,000 grams of toluene. Heat to 115 C. to remove azeotropically any water and 200 ml of toluene. The temperature is reduced to 85 C. and 3.5 ml of 3% $H_2PtCl_6$ in ethanol is added. Light is then excluded from the flask by covering it with a black cloth. An exotherm is noted to about 95 C., while the contents are stirred for about 2 hours. During this time silanic hydrogen concentration drops to nil. Cool to 65 C. and slowly add 60 g of sodium bicarbonate. Allow to mix overnight and filter through a 4 micron pad. Distill off any toluene at 100 C. and 1 torr.

EXAMPLE 5–10

The above procedure is repeated, only this time replacing both the silanic hydrogen compound #3 with the specified number of grams of the specified silanic hydrogen compound and the vinyl intermediate example A with the specified number of grams of the specified vinyl intermediate.

| Example | Vinyl Intermediate Example | Grams | Silanic Hydrogen Compound Example | Grams |
|---|---|---|---|---|
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

ESTERIFICATION

The reaction is generally run with an esterification catalyst. It can be run catalyst free, only protracted reaction times will result.

GENERAL PROCEDURE

The specified amount of hydroxy silicone compound (Examples 4–10) is added to a suitable reaction vessel. The specified amount of monochloro acetic acid is then added along with 0.2% of stannous oxylate catalyst. The reaction mass is then heated to 150–200 C. and is held. The temperature is held until the acid value is vanishingly small. This normally takes 4–6 hours.

| Example | Hydroxy Silicone Example | Grams | Monochloroacetic Acid Grams |
|---|---|---|---|
| 11 | 4 | 740.0 | 97.0 |
| 12 | 5 | 7009.0 | 97.0 |
| 13 | 6 | 943.0 | 97.0 |
| 14 | 7 | 608.0 | 97.0 |
| 15 | 8 | 7771.0 | 97.0 |
| 16 | 9 | 1105.0 | 97.0 |
| 17 | 10 | 2021.0 | 97.0 |
| 18 | 11 | 798.0 | 97.0 |
| 19 | 12 | 7067.0 | 97.0 |
| 20 | 13 | 1001.0 | 97.0 |
| 21 | 14 | 666.0 | 97.0 |
| 22 | 15 | 7829.0 | 97.0 |
| 23 | 16 | 1163.0 | 97.0 |
| 24 | 17 | 2079.0 | 97.0 |

Raw Material Proteins

Proteins useful in the preparation of the products of the present invention are derived from many sources. Many are prepared by the hydrolysis of native proteins. The hydrolysis results in cleavage of some of the polypeptide bonds and increases water solubility. The hydrolysis processes are either acid, alkaline or enzymatic and are well known to those skilled in the art.

Soya Protein (CAS number 68153-28-6); Milk Protein (CAS number 9000-71-9); Wheat Protein; Oat Protein; Vegetable Protein; Keratin Protein (CAS Number 68238-35-7); Placental Protein and Collagen are all sources from which protein is derived.

The proteins useful in the preparation of the compounds of the present invention, in a preferred embodiment range in molecular weight from 1,000 equivalent molecular weight units to 500,000 equivalent molecular weight units. The equivalent molecular weight units are determined by calculation of the free amino groups. An analysis called the "amine value" is run using a standardized acid titrant. The titrations are well known to the fatty chemist and are determined as follows;

$$\text{Amine Value} = \frac{(56.1)\ (\text{normality})\ (\text{ml titrated to pH 5.5})}{(\text{weight in grams of sample})}$$

The amine value is expressed in mg KOH/gm. The amine value is then converted into equivalent molecular weight using the following formula;

$$\text{Equivalent Molecular Weight} = \frac{56{,}110}{\text{Amine Value (mg KOH/gm)}}$$

| Example Number | Commercial Name | Equivalent Weight |
|---|---|---|
| Protein Example A | Peptin 2,000 | 2,054 EMWU |
| Protein Example B | Peptin 5,000 | 5,010 EMWU |
| Protein Example C | Polypro 15,000 | 14,980 EMWU |
| Protein Example D | Peptin AH | 1,500 EMWU |
| Protein Example E | Sollagen | 275,000 EMWU |
| (Peptin, Polupro, and Sollagen are Trademarks of Hormel) | | |
| Protein Example F | Wheat Protein (Hydrolyzed) | 500 EMWU |
| Protein Example G | Wheat Protein | 2,505 EMWU |
| Protein Example H | Oat Protein | 5,560 EMWU |
| Protein Example I | Oat Protein (Hydrolyzed) | 1,000 EMWU |
| Protein Example J | Soya Protein | 15,625 EMWU |
| Protein Example K | Collagen | 500,120 EMWU |
| Protein Example L | Collagen (Hydrolyzed) | 5,250 EMWU |
| Protein Example M | Keratin | 125,750 EMWU |
| Protein Example N | Keratin (Hydrolyzed) | 5,160 EMWU |
| Protein Example O | Placental Protein | 50,450 EMWU |
| (Samples obtained from Phoenix Chemical Inc.) | | |

SILICONE PROTEIN COPOLYMER PREPARATION

General Procedure

To the chloroacetic ester silicone polymer (examples 11-24) is added the specific number of grams of the specified protein reactant (Protein Examples A-O). Water is then added to make the solids 40%.

The resulting reaction mass is heated to 85-90 C. and held for 4-6 hours. The pH is kept or slightly above 7 by additions of small amounts of aqueous base, if needed. The batch clears and the desired silicone based protein is obtained and used without purification. The reaction progress is followed by the percentage of inorganic chloride ion present. The reaction is complete when 97% of theoretical inorganic chloride ion has been generated.

| Example Number | Intermediate Example | Grams | Protein Ex. Number | ** Grams |
|---|---|---|---|---|
| 25 | 11 | 820.0 | A | 1,025 |
| 26 | 12 | 7,098.0 | B | 2,500 |
| 27 | 13 | 1,024.0 | C | 7,500 |
| 28 | 14 | 690.0 | D | 750 |
| 29 | 15 | 7,853.0 | E | 137,500 |
| 30 | 16 | 1,187.0 | F | 250 |
| 31 | 17 | 2,102.0 | G | 1,255 |
| 32 | 18 | 880.0 | H | 2,750 |
| 33 | 19 | 7,149.0 | I | 500 |
| 34 | 20 | 1,083.0 | J | 7,900 |
| 35 | 21 | 748.0 | K | 250,000 |
| 36 | 22 | 7,911.0 | L | 2,800 |
| 37 | 23 | 1,245.0 | M | 72,500 |
| 38 | 24 | 2,161.0 | N | 2,560 |
| 39 | 11 | 822.0 | O | 25,210 |
| 40 | 12 | 7,091.0 | A | 2,054 |
| 41 | 13 | 1,025.0 | B | 5,010 |
| 42 | 14 | 690.0 | C | 14,980 |
| 43 | 15 | 7,853.0 | D | 1,500 |
| 44 | 16 | 1,187.0 | E | 275,000 |
| 45 | 17 | 2,103.0 | F | 500 |
| 46 | 18 | 880.0 | G | 2,505 |
| 47 | 19 | 7,149.0 | H | 5,560 |
| 48 | 20 | 1,083.0 | I | 1,000 |
| 50 | 21 | 748.0 | J | 15,625 |
| 51 | 22 | 7,911.0 | K | 500,120 |
| 53 | 23 | 1,245.0 | L | 5,250 |
| 54 | 24 | 7,161.0 | M | 125,750 |
| 55 | 11 | 822.0 | N | 5,160 |

**Grams of 100% active protein added.

APPLICATIONS EXAMPLES

The compatibility of these novel compounds 90 and 82 with animal tissue was tested. In these tests a 0.1 ml sample of the material being tested was introduced into one eye of an albino rabbit, the other eye serves as a control. Observations were made after 1 day, 2 days, 3 days, 4 days and 7 days. Second and third instillations were made after 24 and 48 hours. Results can vary from substantially no change to complete corneal opacity. Ocular lesions are scored for the cornea, iris and conjuctiva on a scale of 1 to 6 with the higher score indicating graded ocular irritation. The scores are added for the six rabbits tested and an average is obtained. Typical results for the standard quaternary compound used in hair conditioning (stearyldimethylbenzyl ammonium chloride) and a representative of the new compounds being tested are as follows;

| Ocular Irritation | | | | | |
|---|---|---|---|---|---|
| 1 | 2 | 3 | 4 | 7 | |
| | | Days | | | Dermal Irritation |
| Developmental Compound #50 | | | | | |
| 0 | 0 | 0 | 0 | 0 | 0.00 |
| Developmental Compound #55 | | | | | |
| 0 | 0 | 0 | 0 | 0 | 0.00 |
| Comparison Product | | | | | |
| Stearyldimethylbenzyl ammonium chloride | | | | | |
| 34 | 29 | 27 | 26 | 26 | 3.75 |

The data shows dramatically that the novel compounds are very mild, while the standard quaternary used in hair conditioning is a severe irritant.

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Product Example #50 | 10 |
| Product Example #55 | 11 |
| Stearyldimethylbenzyl ammonium chloride | 12 |

The compounds of the present invention are very mild to the skin, eyes and mucous membrane when applied at 10% active.

The compounds of the present invention are not toxic when tested in LD 50 tests.

The compound of the invention are excellent conditioners and antistatic agents. All of these attributes make the compounds of the present invention candidates for use in personal care compositions.

I claim:

1. A silicone protein which is prepared by the reaction of an intermediate conforming to the following structure;

R—O—C(O)—CH$_2$—Cl wherein;

R is 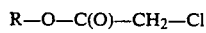

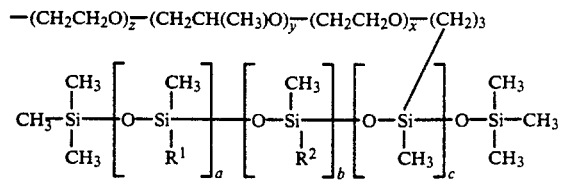

a is an integer from 0 to 200;
b is an integer from 0 to 200;
c is an integer from 1 to 200;
R$^1$ is selected from the group consisting of —(CH$_2$)$_n$CH$_3$ and phenyl;
n is an integer from 0 to 10;
R$^2$ is —(CH$_2$)$_3$—(OCH$_2$CH$_2$)$_x$—(OCH$_2$CH(CH$_3$))$_y$—(OCH$_2$CH$_2$)$_z$—OH;
x, y and z are integers and are independently selected from 0 to 20;
with a protein.

2. A silicone protein of claim 1 wherein b is zero.

3. A silicone protein of claim 1 wherein x, y and z are all zero.

4. A silicone protein of claim 1 wherein the molecular weight of the protein ranges from 1,000 molecular weight units to 500,000 molecular weight units.

5. A silicone protein of claim 1 wherein the molecular weight of the protein ranges from 1,000 molecular weight units to 50,000 molecular weight units.

6. A silicone protein of claim 1 wherein the molecular weight of the protein ranges from 10,000 molecular weight units to 20,000 molecular weight units.

7. A silicone protein of claim 1 wherein the protein is a wheat based protein.

8. A silicone protein of claim 1 wherein the protein is a soy based protein.

* * * * *